United States Patent [19]

McLaughlin et al.

[11] 4,346,599
[45] Aug. 31, 1982

[54] METHOD AND APPARATUS FOR ULTRASONICALLY TESTING POLYMERS

[75] Inventors: Albert J. McLaughlin, Lancaster; Gary W. Paddison, Dover, both of Pa.

[73] Assignee: Armstrong World Industries, Lancaster, Pa.

[21] Appl. No.: 184,786

[22] Filed: Sep. 8, 1980

[51] Int. Cl.³ .......................................... G01N 29/00
[52] U.S. Cl. ................................................. 73/597
[58] Field of Search ............... 73/597, 599, 618, 632, 73/633, 644; 250/231 SE

[56] References Cited

U.S. PATENT DOCUMENTS

| | | | |
|---|---|---|---|
| 2,751,783 | 6/1956 | Erdman | 73/644 |
| 3,646,806 | 3/1972 | Yamaguchi et al. | 73/644 |
| 3,858,437 | 1/1975 | Jarzynski et al. | 73/67.5 R |
| 3,938,372 | 2/1976 | Sproule | 73/644 |
| 4,020,679 | 5/1977 | Barry | 73/644 |
| 4,279,157 | 7/1981 | Schomberg et al. | 73/618 |

OTHER PUBLICATIONS

Gary W. Paddison, "An Ultrasonic Immersion Apparatus for the Determination of High-Frequency Storage and Loss Moduli for Polymers and Polymeric Composites", Ultrasonics Symposium Proceedings, Sep. 1979.
J. R. Asay, D. L. Lamberson, and A. H. Guenther, *J. Appl. Phys.*, 40, 1968, 1969.
J. Williams and J. Lamb, *J. Acoustic Soc. Am.*, 30, 308, (1958).
G. W. Paddison, *Polym. Eng. & Sci.*, 14, 382, (1974).
H. A. Waterman, *Kolloid-Zeitschrift and Zeitschrift fur Polymere*, 192, 1, (1963).
B. Hartmann and J. Jarzynski, *J. Acoust. Soc. Am.*, 56, 1469, (1974).
B. Hartmann and J. Jarzynski, *Naval Ordnance Laboratory* TR72-73, 1973.
D. Ensminger, "Ultrasonics – The Low and High-Intensity Applications", p. 38, Marcel Dekker, Inc., New York, (1973).
E. U. Condon and H. Odishaw, "Handbook of Physics", pp. 3-12, McGraw Hill, Inc., New York, (1958).
Z. Ribgi, *Appl. Poly. Symposia*, 5,1, (1967).

*Primary Examiner*—Stephen A. Kreitman
*Attorney, Agent, or Firm*—Woodcock, Washburn, Kurtz, Mackiewicz & Norris

[57] ABSTRACT

Apparatus for ultrasonically testing polymer materials includes means for measuring the thickness of the specimen and for measuring the mass density of the specimen in situ. Ultrasonic measurements of the specimen are obtained. Then the specimen holder is rotated past the critical angle and new ultrasonic measurements are obtained. From these ultrasonic measurements the storage and loss moduli and attenuation coefficients for the polymer specimen are obtained.

25 Claims, 9 Drawing Figures

METHOD AND APPARATUS FOR ULTRASONICALLY TESTING POLYMERS

BACKGROUND OF THE INVENTION

This invention relates to the testing of specimens of polymer material and more particularly to the determination of high frequency dilatational and shear velocities, storage and loss moduli and attenuation coefficients for polymer materials.

Ultrasonic testing of polymer materials is conventionally carried out by a buffer-rod technique, such as that described in J. R. Asay, D. L. Lamberson, and A. H. Guenther, *J. Appl. Phys.*, 40, 1768 (1969); J. Williams and J. Lamb, *J. Acoust. Soc. Am.*, 30, 308 (1958); and G. W. Paddison, *Polym. Eng. & Sci.*, 14, 382 (1974). While accurate, the technique does not provide a complete characterization (except for transition temperature) because of the wave-propagation mode. Due to the high coupling losses in shear-wave transducers, with this technique the only wave mode that can be propagated in polymers at temperatures above the α-transition is the dilatational mode, and the dilatational modulus M from this mode is a composite of the bulk K and shear G moduli. A measurement in another wave mode is required in order to determine the individual moduli of the polymers. (As used herein, polymer materials include polymers and polymeric composites).

Ultrasonic immersion apparatus for measuring both the dilatational and shear velocities in solid specimens is known. A system for rotating the specimens to exceed the critical angle is described in H. A. Waterman, *Kolloid-Zeitschrift and Zeitschrift Fur Polymere*, 192, 1 (1963). This technique can be used for measurements on metals and room temperature measurements of polymers. However, because polymers become rubbery and can be deformed above the glass transition temperature, such an apparatus cannot be used for temperature dependent measurements at elevated temperatures. The rotation of the specimens by the apparatus is unacceptable above the glass transition temperature because the specimens may be deformed.

U.S. Pat. No. 3,858,437 Jarzynski et al. shows an apparatus in which the transducers are rotated about a stationary specimen. The present invention relates to improvements in this type of apparatus which make it possible to measure the high frequency storage and loss moduli for polymer materials.

The ultrasonic measurement technique described in the aforementioned Jarzynski et al. patent and in the articles B. Hartmann, and J. Jarzynski, *J. Acoust. Soc. Am.*, 56, 1469 (1974); and B. Hartmann, and J. Jarzynski, *Naval Ordnance Laboratory TR*72-73, (1973) is a so-called "slope" measurement technique. The measurements made with Jarzynski et al. apparatus were limited to a narrow range of temperatures. In this technique different specimens having substantial differences in thickness are acoustically tested. Such a technique cannot be used on polymer specimens at temperatures above the glass transition temperature or at high frequencies. Very thin specimens of polymer material must be used in wide-range temperature dependent acoustic testing. So much energy is absorbed in the specimen that thick samples absorb all of the acoustic energy. Since it is necessary to determine the acoustic insertion loss property above the glass transition temperature, thin specimens which do not absorb all of the acoustic energy must be used. Also, in measurements such as those carried out by Jarzynski et al., the mass density of the specimen is measured at room temperature and it is assumed to remain constant throughout the measurements. This is not a valid assumption for polymers which have a mass density with a significant dependence upon temperature. Since the storage moduli of polymers are related to mass density, which is dependent upon temperature, provision must be made for measuring mass density at each of the temperatures at which acoustic measurements are made. Furthermore, the same polymer material may have a different mass density from specimen to specimen depending upon the rate of heating the specimens. Some polymers have atomic sized air voids which expand at different rates depending upon the rate of heating or cooling. Even if the specimens are heated at a constant rate, there is a geometry effect by which mass density at a particular temperature may depend on the shape of the specimen.

Another physical characteristic of polymers which is temperature dependent is specimen thickness. The specimen thickness is a parameter in the determination of storage and loss moduli. It may vary considerably if measurements are made over a wide range of temperatures.

It is an object of the present invention to provide an automated, ultrasonic immersion apparatus and method that measures dilatational and shear velocity, storage and loss moduli, and attenuation over a wide temperature range.

SUMMARY OF THE INVENTION

In accordance with the present invention, temperature dependent physical characteristics including the mass density and thickness of a polymer specimen are measured in situ at each temperature at which ultrasonic measurements are made.

The ultrasonic measurements are made with a transmitting and a receiving transducer properly oriented on opposite sides of the specimen which is immersed in a sound conducting fluid. The measurements include electronically measuring the transit time of an acoustic wave between the transmitting transducer and the receiving transducer. Then the transducers are rotated about an axis between the transducers and the transducers are reoriented relative to the specimen. The transducers are rotated to exceed the critical angle at which the dilatational mode wave is not transmitted through the specimen. Above the critical angle, the measured transit time of an acoustic wave represents shear velocity. From the measured shear and dilatational velocities, incident angle, thickness and mass density, the storage moduli of the specimen are determined. The storage moduli are plotted as a function of different temperatures at which the measurements are made in order to completely characterize the properties of the polymer specimen.

In accordance with one feature of the present invention, the ultrasonic measurement apparatus includes a manometer for measuring the volume of a specimen at each temperature at which measurements are made. From the measured volume and weight of the specimen, the mass density can be determined in situ.

Further in accordance with the invention, the apparatus includes probes for automatically measuring the thickness of each specimen mounted in specimen holders in a rotatable support surface.

Further in accordance with the present invention, rotation of the transducers about the specimen is effected by a first electronic motor. A second electric motor reorients the transducers one with respect to the other by counter-rotating them in planes parallel to the axis of rotation. An alignment detector is provided to indicate alignment of the transducers.

The foregoing and other objects, features and advantages of the invention will be apparent from the drawings, description of the preferred embodiment, and appended claims.

SHORT DESCRIPTION OF THE DRAWINGS

FIG. 3 shows the transducers after they have been reoriented with respect to the specimen;

DESCRIPTION OF THE PREFERRED EMBODIMENT

Figure 1:
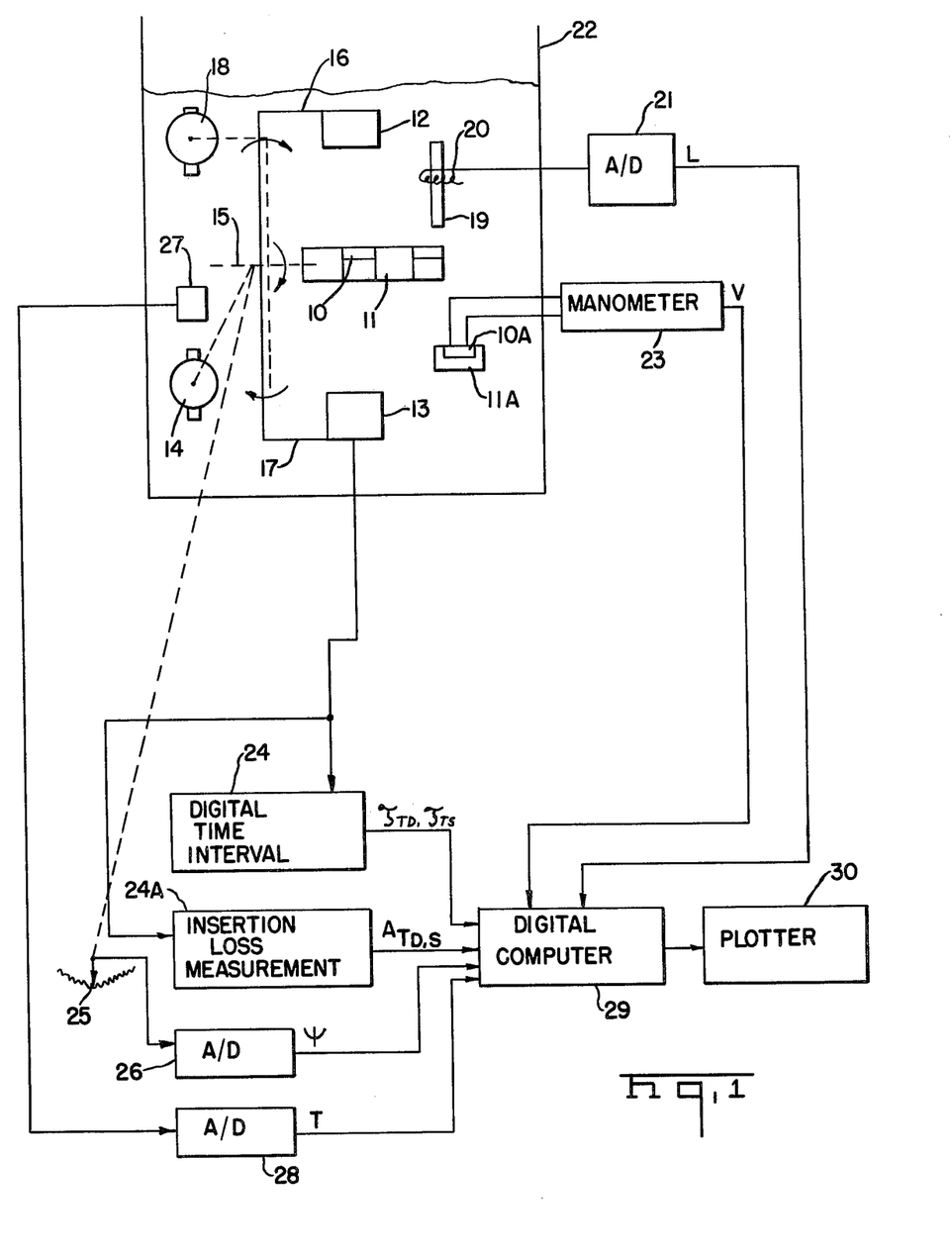
FIG. 1 depicts the apparatus of this invention.
Figure 2:
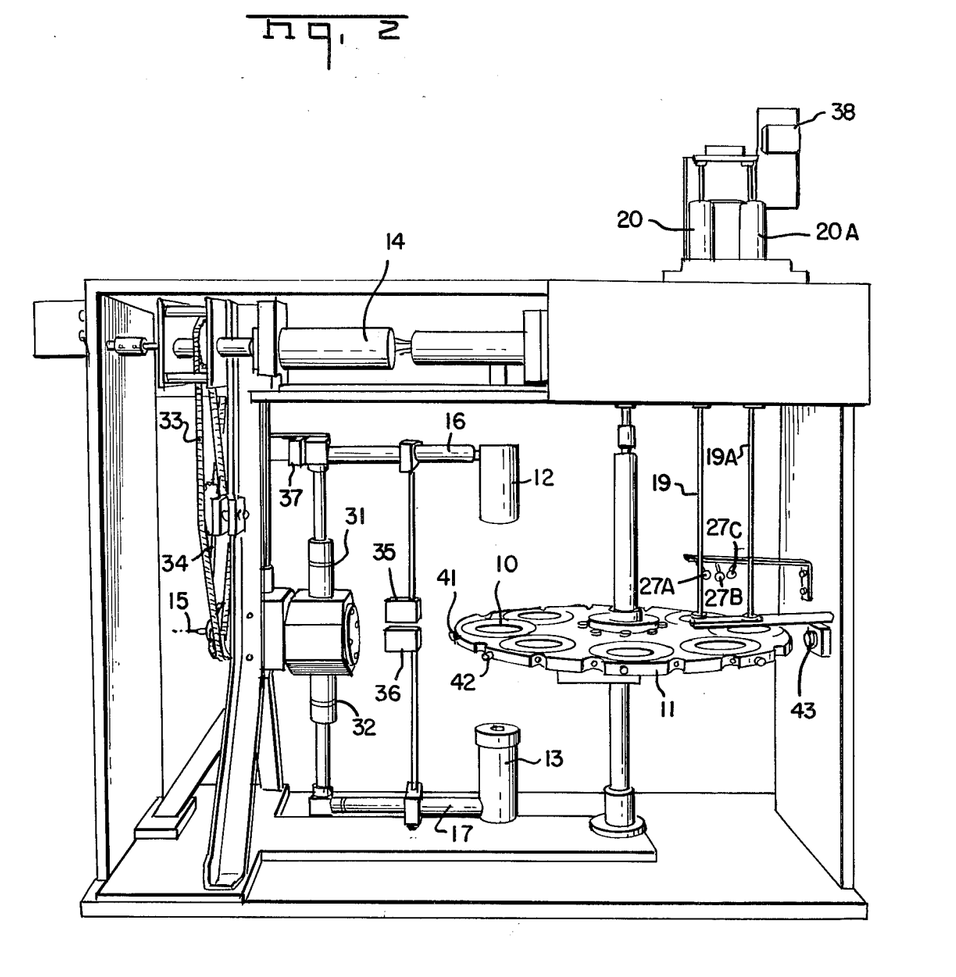
FIG. 2 shows the transducers and rotating support surface for the specimen holders.

Referring to FIGS. 1 and 2, the apparatus of the present invention includes a plurality of specimen holders such as 10 which are mounted on a rotating support table 11. A first ultrasonic transducer 12 transmits ultrasonic energy through the specimen. A second ultrasonic transducer 13 detects the energy transmitted through the specimen.

The transducers 12 and 13 are contained in fluid-tight containers having a removable closure and a polymer gasket. One example of a polymer material suitable for use is Dow-Corning Silastic-675 Fluorosilicone polymer. Solderless connectors are provided in each of the containers for making quick electrical connections to the transducers. In this manner, the transducers can be easily changed for making different frequency measurements. A series of torroidal inserts adapt transducers of different diameters to the inside diameter of the container.

The transducers are supported in opposed orientation with the specimen holder between them. Normal incidence of the ultrasonic wave is obtained with the transducers in the position shown in FIGS. 1 and 2.

A first electric motor 14 rotates the transducers about an axis 15 which is between the transducers. Transducer 12 extends orthogonally from a first arm 16 and transducer 13 extends orthogonally from a second arm 17. The transducers 12 and 13 and the arms 16 and 17 are initially in the same plane. After the transducers have been rotated about the axis 15, the transducers are reoriented by counter-rotating the arms 16 and 17. This type of mechanism for rotating the transducers with respect to the specimen and then counter-rotating them for reorientation is described in the aforementioned Jarzynski patent. The present invention is an improvement on that apparatus in that the first electric motor 14 rotates the transducers about the axis 15 and a second electric motor 18 counter-rotates the arms 16 and 17 for reorientation.

The apparatus described thus far is mounted in a tank 22 which is filled with a sound conducting fluid. In order to measure the characteristics of polymers over a broad range of temperatures it is preferable to use a low loss, low velocity, low viscosity immersion fluid which has a low viscosity/temperature coefficient. One fluid which has been found particularly suitable for use is a silicone fluid such as Dow-Corning XF1-3755. This fluid has a low acoustic velocity characteristic of approximately 910 m/s, and a low viscosity of approximately 10 cp.

The fluid is maintained at desired temperatures by high and low wattage electric immersion heaters for heating and a solenoid controlled, liquid nitrogen, immersion heat exchanger and a defrosting device for cooling. These devices, not shown in the drawings, are controlled by a solid state temperature controller.

In accordance with the present invention, provision is made for measuring in situ temperature dependent characteristics of the specimen including thickness and mass density of the specimen at each temperature at which acoustic measurements are made. A probe 19 and a differential transformer 20 produce an electrical signal representing the specimen thickness L. This signal is digitized as indicated by the analog/digital convertor 21 (FIG. 1).

As shown in FIG. 2, the device for measuring the temperature dependence of specimen thickness in situ includes the probes 19 and 19a. A cam rotates to a position at which the probes 19 and 19a drop into contact with the surface of the specimen at two points. A switch 38 is actuated when the probes are in the measurement position.

A manometer 23 is selectively connected to each of the mass density specimen holders on the support surface 11A to measure mass density in situ. Each mass density specimen holder, such as 10A, holds a specimen of the same material as the specimen in the corresponding specimen holder, such as 10. The manometer 23 produces an output representing the volume of the specimen in specimen holder 10A. The specimen is weighed prior to testing. The mass density at each temperature is determined from weight/volume.

The acoustic measurements include measurements of the transit time of an acoustic wave from the transmitting transducer 12 to the receiving transducer 13; a digital time interval unit 24 digitizes the time interval $\tau_{TD}$ which represents the total transit time of the dilatational wave and $\sigma_{TS}$ which represents the total transit time of the shear wave.

Measurement of the incident angle $\psi$ is necessary for the determination of the storage and loss moduli for polymers. In accordance with the present invention, a potentiometer 25 is rotated as the transducers are rotated to exceed the critical angle. Above the critical angle, the output of the potentiometer 25 represents the incident angle $\psi$. This signal is digitized as indicated by the analog/digital convertor 26.

The other measurement required for complete characterization of the polymer specimens is temperature. A thermocouple 27 is immersed in the fluid. Its output is digitized as indicated by the analog/digital convertor 28.

All of the signals representing measurements are applied to a digital computer 29 which generates signals representing the storage and loss moduli for the polymers being tested. These are plotted as functions of temperature on the plotter 30.

In FIGS. 1 and 2 the arms 16 and 17 are in the same plane with the orthogonally extending transducers 12 and 13. In this normal incidence position, measurements of the transit time of the dilatational wave are made.

FIG. 3 shows the transducers rotated about the axis 15 for measurement of the transit time of the shear wave. The arms 16 and 17 have been counter-rotated one with respect to the other to reorient them with the specimen holder. The arm 16 rotates at the joint 31 and the arm 17 rotates at the joint 32. The joints 31 and 32 include Teflon bushings to facilitate easy rotation.

The first electric motor 14 is connected through the drive chain 33 to rotate the carriage about the axis 15. The second electric motor is behind the motor 14 in FIG. 2 and is not shown. The second electric motor drives the chain 34 which counter-rotates the arms 16 and 17 at the joints 31 and 32. The mechanism for effecting counter-rotation of the arms is similar to that described in the aforementioned Jarzynski patent.

In prior art apparatus such as that shown in Jarzynski et al., there is mechanical slip when the transducers are being rotated about the axis. Because of this mechanical slip the transducers are misaligned with respect to the specimen after rotation. In accordance with the present invention, this mechanical slip, and consequent misalignment, is obviated by running the second motor 18 in reverse while the motor 14 is rotating the transducers.

FIGS. 2 and 3 show the alignment detector which includes the light source 35 and the photodiode 36. After the transducers have been re-rotated it is necessary to have alignment of each of the transducers from center to center with the line between them extending through the specimen. The maximum response of the transducer is in the center so it is important to always operate with this type of alignment. The alignment detector facilitates this alignment.

The photodiode 36 is in a casing which has a pinhole. When the transducers are precisely aligned, center to center, the light from the source 35 passes through the pinhole to the photodetector. This produces an electrical output signifying alignment. The provision of this alignment system gives an important advantage over the prior art. In using prior art apparatus of the type shown in Jarzynski et al, the realignment was accomplished by observing an oscilloscope displaying the output of the received transducer. The transducers were recounter-rotated until the output of the receiver approximately matched the output when the transducers were originally opposed and orthogonal to the sample. Since this was not very accurate, measurements were continuously made without the specimens at each different temperature for each given re-alignment. This is time consuming because each variation in temperature requires a significant time for re-establishing the immersion fluid calibration attenuation. On the other hand, with the apparatus of the present invention, it is possible to make a number of measurements at each temperature. With the alignment device of this invention, the transducers can be automatically realigned for each angle of rotation.

In order to indicate when the transducers and the arms carrying them are re-rotated to the vertical plane alignment shown in FIG. 2, a switch 37 is actuated by the arms.

In order to make measurements on a number of different samples, the rotatable support surface 11 accommodates up to eight specimen holders. As the support surface 11 is rotated, alignment pins on the bottom of the support surface engage the switch 39 (FIG. 3). These pins, one of which is indicated at 40, are aligned with the specimen holders so that when the switch 39 is actuated, the specimen is in correct alignment with the transducers 12 and 13. Alignment pins such as 41, 42, and others are provided around the periphery of the rotating support surface 11. These alignment pins actuate a switch 43 (FIG. 2) to indicate alignment of the sample holder with the probes 19 and 19a so that measurements of specimen thickness can be made.

Figure 4:
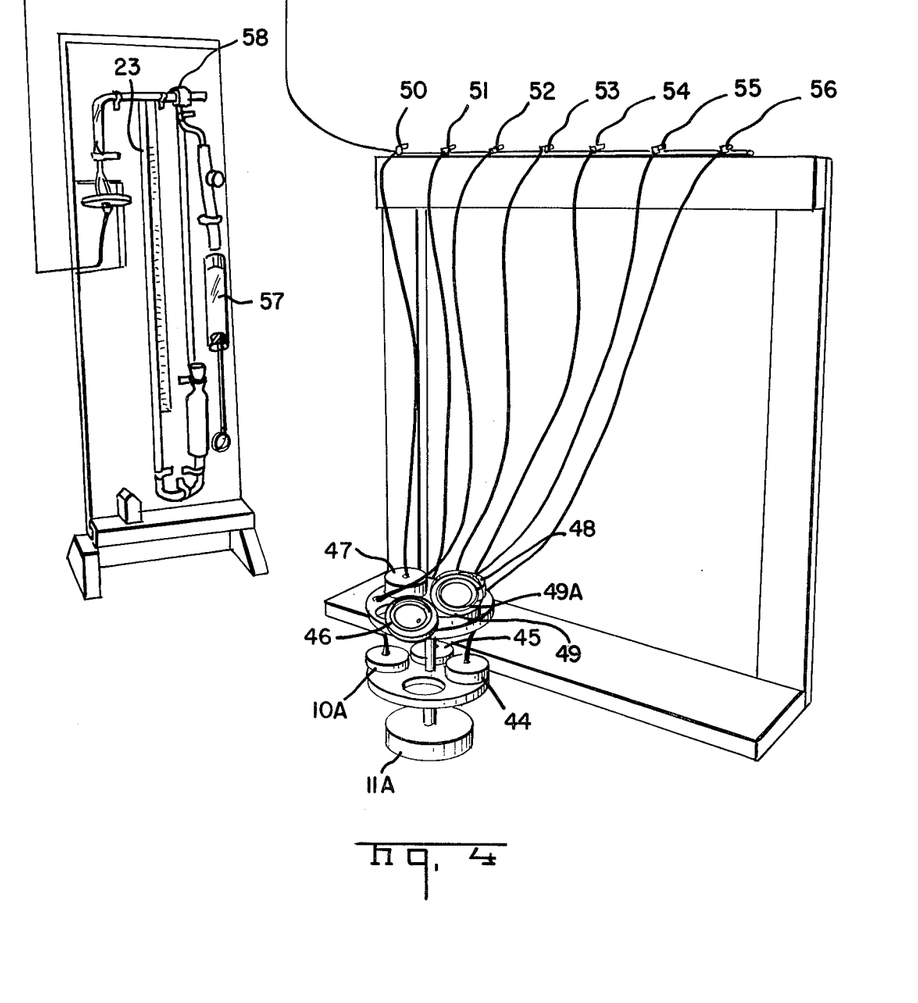
FIG. 4 shows the manometer connected to the specimen holders.

The manometer for measuring specimen volume (mass density) is shown in FIG. 4. Each specimen holder includes a gasket such as 49A of a suitable material such as Dow-Corning Silastic-675 Fluorosilicone polymer. Each specimen holder can accommodate a specimen 35 mm in diameter.

Each of the mass density specimen holders 10A, 44-49 is connected through plastic tubing to one of the stop cocks 50-56. These selectively connect a specimen holder to the manometer 23. The other end of the manometer 23 is connected to a piston 57. A stop cock 58 selectively connects this end of the manometer to either the piston 57 or to the atmosphere.

The operation of the mass density measurement apparatus is as follows. Before the specimens are inserted, each specimen holder is closed. Its temperature dependent volume is measured by pressurizing it by pumping the piston 57. A reading is taken from the manometer 23 and then the stop cock 58 is opened to the atmosphere. A second reading is taken and the difference in the readings indicates the volume of the specimen holder. When the specimens are inserted and the holders are placed in situ in the immersion fluid, readings can again be taken in a similar manner at different temperatures. The difference between the original reading and the reading in situ indicates the volume of the specimen at that temperature. As previously discussed, this volume measurement is used in the determination of mass density.

In accordance with another aspect of this invention, provision is made for automatically cleaning bubbles from the transducer and for mechanically stirring the liquid to eliminate interference caused by mechanical effects such as bubbles and small thermal gradients. In the prior art apparatus, such as that disclosed in the Jarzynski, et al patent, small bubbles collect on the underside of the specimen. These interfere with ultrasonic measurements. These bubbles are created as a result of high speed agitation of the immersion fluid during a temperature change. Air is entrained at the fluid to air interface. In the prior art, this problem is generally solved by periodically wiping the bubbles off the transducer mechanically. The temperature drops when this is done, and as a result, equilibrium is never obtained. This is not acceptable in the measurement of polymer material characteristics.

In accordance with the present invention, a ring collar 71 is positioned over the top transducer 12 to debubble and stir the fluid in the vicinity of this transducer. The ring collar 71 is shown in more detail in FIG. 4A. Vacuum couplings 72 and 73 are connected to a source of vacuum. The vacuum coupling terminates in a thin metal tube bent at a right angle to the fitting and which extends to the surface of the transducer, where it is again bent at a right angle to protrude to the edge of the transducer. When vacuum is applied, bubbles are sucked from the surface of the transducer, thereby preventing any interference.

Figure 4A:
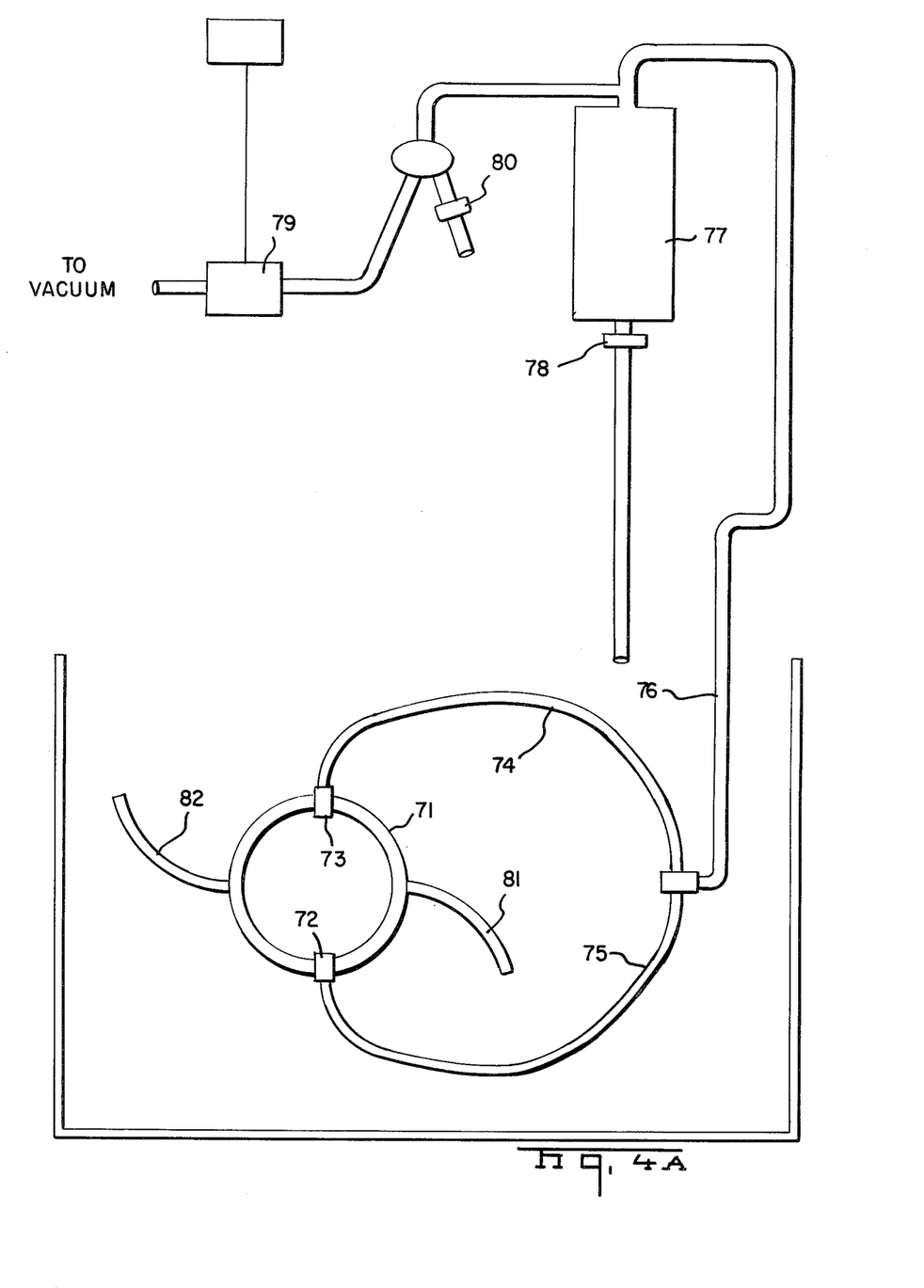
FIG. 4A shows the automatic debubbling device for cleaning the top transducer.

In order to apply vacuum to the couplings 72 and 73, they are connected through hoses 74, 75, and 76 to a catch basin 77 which permits fluid drawn off by the suction to be debubbled and returned through a stop cock 78 to the tank. An electric solenoid valve 79 is actuated to apply vacuum when the system is in operation. A stop cock 80 provides an air bleed for the system.

In accordance with another important feature of the present invention, baffles 81 and 82 on the ring collar create an eddy between the transducers during a very mild agitation to eliminate small thermal gradients when the low wattage immersion heater is on. The bottom transducer 13 has a similar ring collar with the baffles, but without the debubbling vacuum couplings. Accumulation of bubbles on the lower transducer is not a problem since all bubbles rise.

Figure 6:
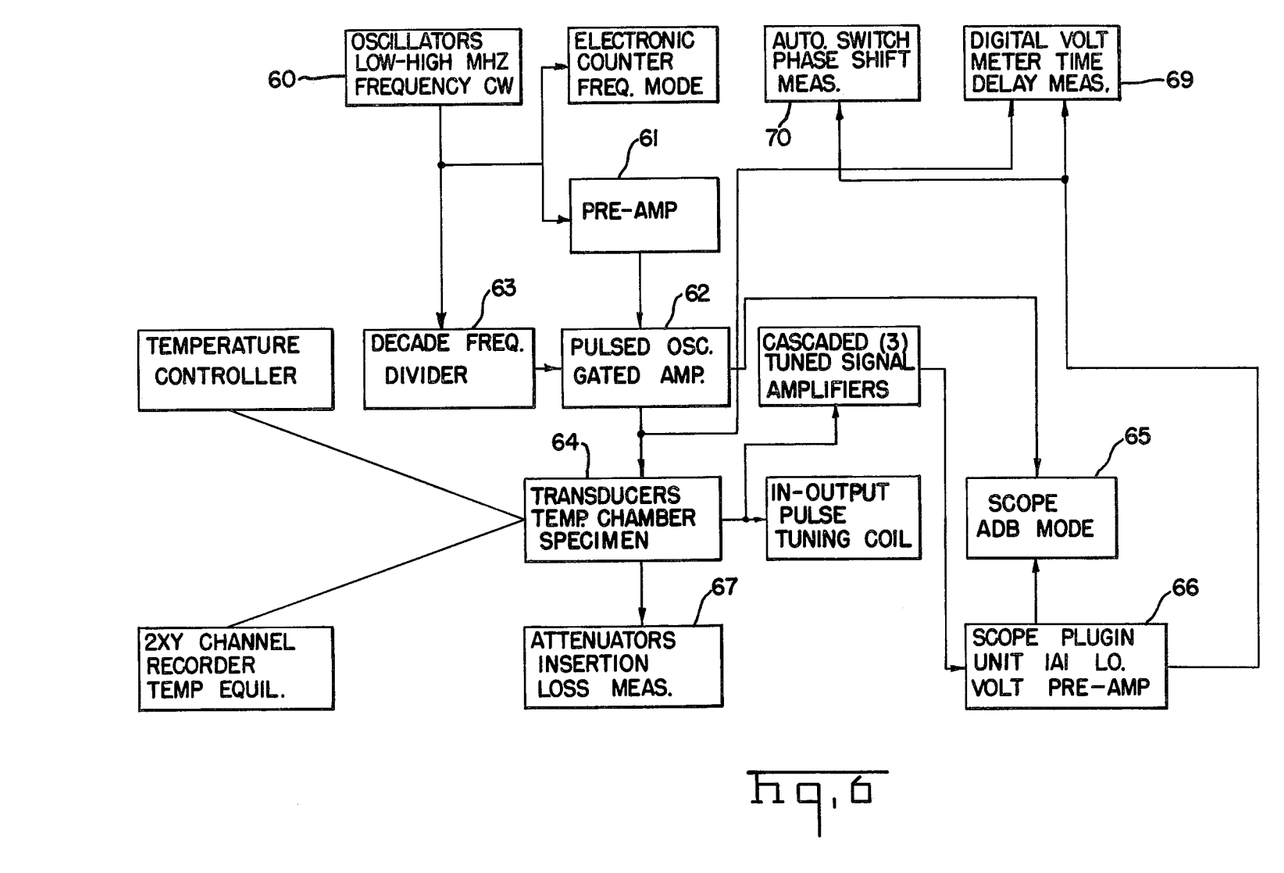
FIG. 6 is an electronic block diagram.

A block diagram of the electronic system is shown in FIG. 6. A continuous wave oscillator 60 drives pre-amp 61 which in turn drives the pulsed oscillator 62 operating in a gated amplifier mode. This produces coherent sinusoidal pulses that begin and end on the zero crossing of the sine wave. Coherence is produced by using the continuous wave signal from oscillator 60 to drive a frequency divider 63 which in turn triggers the pulsed oscillator 62. The gated amplifier 62 produces a pulsed RF output which drives the transducers indicated at 64. The output of pulsed oscillator 62 also triggers the oscilloscope 65 which has a dual trace plug-in unit 66.

The insertion loss attenuation of the specimen is measured by using low capacitance step attenuators 67. By use of comparison techniques the attenuation of the specimen is obtained. This eliminates the resolving of multiple echo patterns and the phase problems associated with the reverberation of the echoes. In one particular example, the attenuators 67 had three matched cascaded variable amplifiers and a constant, low loss, automatic switching device to eliminate spurious harmonic distortion and unknown phase shifts. The measurements were made by setting the received pulse at a prescribed amplitude on the oscilloscope and then attenuating the transmitted pulse by the step attenuators.

The pulse transit-time is measured with an electronic time-interval unit including digital voltmeter 69 and automatic phase-shift measurement circuit 70. The measured transit-time delay is averaged over $10^5$ pulses. This eliminates the phase-shift interference, which can be a source of error with polymeric samples. The triggering pulses for the time-interval unit are taken from the transmitted wave at the RF output and the received wave from the oscilloscope. The received wave is amplified by a factor of 10 by using channel 1 of the plug-in unit 66. The tap for the triggering pulse is taken here because a d.c. block, which is used for the attenuation measurements, is also required to prevent jitter in the time-delay measurements. A constant triggering voltage of 200 mv is required for accurate time-delay measurements. Therefore, the amplified voltage was adjusted by using the variable cascaded amplifiers in the attenuators 67. The triggering voltage was monitored with a digital voltmeter in-line with the time-interval unit. The resolution is 100 ps.

Figure 5:
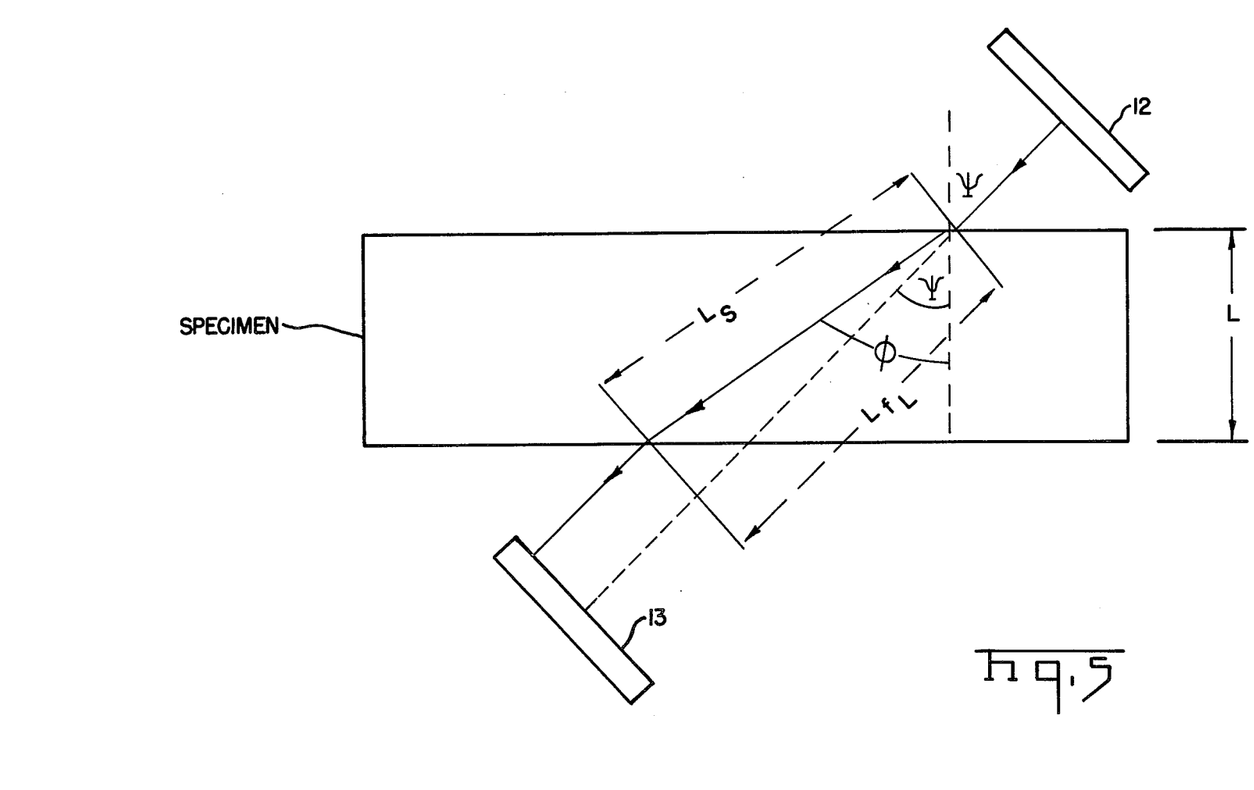
FIG. 5 depicts the geometry of shear wave propagation.

The operation of the system in making measurements is as follows. For each specimen, measurements are made at normal incidence, that is with the transducers in the position shown in FIG. 2. At normal incidence, the transit time $\tau_{TD}$ and the attenuation $A_{TD}$ are measured. A measurement is made of temperature T and of the specimen thickness L and volume V. Then the motor 14 is energized to rotate the specimen to exceed the critical angle. The critical angle is determined by observing the oscilloscope 65. When the amplitude of the received acoustic wave drops significantly, and is down shifted in time-domain, the critical angle has been reached. This is the angle at which the dilatational wave (sometimes called the longitudinal wave) is completely internally reflected. Above this angle only the shear wave is transmitted through the specimen. The geometry of the shear wave propogation at the critical angle is shown in FIG. 5. Above the critical angle, measurements are made of the attenuation $A_{TS}$ and of the transit time $\tau_{TS}$. A measurement of incident angle $\psi$ is made. All measurements are inputted to the digital computer 29. The foregoing measurements are repeated for different temperatures.

The manner of determining the storage and loss moduli and the attenuation coefficients for the polymers is described below in a manner which is computer oriented. The manner of operating the computer 29 to make these determinations will be apparent.

The dilatational modulus M is a composite of the bulk K and shear G moduli as in:

$$M = K + 4/3 G. \tag{1}$$

The equation cannot be resolved in terms of the individual moduli from the dilatational wave alone. I have found that by using nontuned transducers, a second wave mode—the shear mode—is simultaneously propagated with the normal dilatational wave mode. By applying Snell's law, Equation 2, the two wave modes can be isolated:

$$\sin \psi / \sin \phi = V_L / C_S \tag{2}$$

where $\psi$ = angle of incidence; $\phi$ = angle of refraction; $V_L$ = dilatational velocity of the fluid phase; and $C_S$ = shear velocity of the solid specimen.

The necessary requirements are that: (1) the solid specimen must be immersed in a low-loss and nearly inert fluid and (2) at all temperatures the dilatational velocity $V_L$ in the fluid phase must be less than the dilatational velocity $C_D$ in the solid phase. At normal incidence the dilatational mode is propagated in the specimen. The shear mode can be isolated by changing the incident angle to exceed the critical angle $\psi_C$ for internal reflection of the dilatational wave as in:

$$\psi_C = \sin^{-1}(V_L/C_D) \tag{3}$$

As previously discussed, the occurrence of the critical angle is viewed on an oscilloscope as an abrupt shift in the displayed pulse.

All calibration data for the ultrasonic immersion apparatus and the immersion fluid were previously measured over the system temperature range and reduced to equation form.

Velocities

The determinations of the dilatational velocity is as follows. At normal incidence the dilatational velocity $C_D$ is calculated from the specimen thickness L, the total transit time $\tau_{TD}$, the calibration transit-time $\tau_C$, and the immersion fluid velocity $V_L$ according to $$C_D = L[\tau_{TD} - (\tau_C - L/V_L)]^{-1} \quad (4)$$

The calculation of the shear velocity is more complex. Because of the wave refraction at incidence angles other than normal, the shear-wave path length $L_S$ is not the same as the actual specimen thickness L. The shear-wave path length $L_S$ can be calculated from the total transit time, the calibration transit time, the specimen thickness, the fluid velocity, and the incident angle $\psi$ by applying Snell's law according to Equation 2:

$$L_S = L[1 - (A \sin \psi)^2]^{-\frac{1}{2}} \quad (5)$$

where $A = [(\cos \psi - V_L(\tau_C - \tau_T)/L)^2 + \sin^2 \psi]^{-\frac{1}{2}}$ The effective path length of the displaced immersion fluid $L_{fl}$ can be calculated from the shear-wave path length, the incident angle, and the refraction angle $\phi$ according to $$L_{fl} = L_S \cos(\phi - \psi) \quad (6)$$

where $\phi = \cos^{-1}(L/L_S)$.

Finally, the shear velocity $C_S$ is calculated by $$C_S = L_S[\tau_{TS} - (\tau_C - L_{fl}/V_L)]^{-1} \quad (7)$$

For lossy polymeric specimens, generally only one short path length can be used. The calculation of the attenuation coefficients is more complex than the calculation of the moduli. The measured parameter for each wave mode (D,S) is the total attenuation $A_T$. For lossy specimens, the following series of equations is required for the calculation of the dilatational-wave $\alpha_D$ and shear-wave $\alpha_S$ attenuation coefficients.

The attenuation coefficients per unit length $\alpha_D$, $\alpha_S$ are calculated from the total attenuation $A_T$, the calibration attenuation $A_C$, the immersion-fluid attenuation $\alpha_{fl}$, the impedance mismatch loss ML, and the specimen thickness according to Equation 8:

$$\alpha_D, \alpha_S = [A_{TD,S} - (A_C - \alpha_{fl} L_{fl}) - ML_{D,S}]/L \quad (8)$$

For the shear wave the shear path length $L_S$ is used.

For the dilatational wave the impedance mismatch loss $ML_D$ is calculated from the specimen impedance $Z_D$ and the immersion-fluid impedance $Z_L$ by Equation 9:

$$ML_D = 8.686 \, Ln |[(Z_D + Z_L)^2 / 4 Z_D Z_L]| \quad (9)$$

For the shear wave, the impedance-mismatch loss $ML_S$ is more complicated, because of the need to calculate the wave-reflection coefficient at any incident angle other than normal. A general solution to the shear mode is available. The impedance-mismatch loss can be calculated from the incident angle, the refraction angle, the dilatational-wave specimen impedance, the shear-wave specimen impedance $Z_S$, and the immersion-fluid impedance by Equation 10:

$$ML_S = 8.686 \, Ln \left| \left[ \frac{[Z_D \cos 2\phi \cos(\psi - \phi)] + A}{[Z_D \cos 2\phi \cos(\psi + \phi)] + A} \right] \right| \quad (10)$$

where $A = (2 Z_S \sin \psi \sin \phi + Z_L) \cos \phi$.

The specimen impedances can be calculated from the dilatational and shear velocities, and the specimen mass density $\rho$.

The equations for determining specimen attenuation coefficients are a set of transcendental equations which are solved by a computer iteration technique. Specimen impedances for polymers:

$$Z_D = \left( \frac{(\zeta C_D)^2}{1 + \xi_D^2} \right)^{\frac{1}{2}} ; Z_S = \left( \frac{(\zeta C_S)^2}{1 + \zeta_S^2} \right)^{\frac{1}{2}} \quad (11)$$

where
$\xi_D = \alpha_D C_D / 8.686 \, \omega$
$\xi_S = \alpha_S C_S / 8.686 \, \omega$
where $\xi_D = \alpha_D C_D / 8.686 \, \omega$, with $\omega$ = angular frequency. $\quad (11A)$ For liquid immersion fluid impedance, $Z_L = \zeta_L V_L$. For elastic solids and liquids, the elastic damping factor is near zero whereas for polymers, it has a significant value. Therefore, this simpler expression can be used for liquid immersion fluid impedance. Equations 8, 9, 11 and 11A must be solved implicitly by a computer iteration technique with a cut-off criterion of $1 \times 10^{-4}$.

For the shear mode Equations 8, 10, 11 and 11A must also be solved implicitly by a computer iteration technique with a cut-off criterion of $1 \times 10^{-4}$. The immersion-fluid impedance is calculated from the fluid velocity and mass density $\rho_L$ in a like manner.

Dilatational and Shear Moduli

With the determination of the velocity and attenuation coefficients, the calculation of the storage and loss moduli is straightforward. The dilatational storage $M'$ and loss $M''$ are calculated from the dilatational velocity, the dilatational damping factor $\xi_D$, and the specimen mass density:

$$M' = \rho C_D^2 [(1 - \xi_D^2)/(1 + \xi_D^2)^2] \text{ and} \quad (12)$$
$$M'' = 2 \rho C_D^2 [\xi_D/(1/(1 + \xi_D^2)^2], \quad (13)$$

The shear moduli are calculated in an analogous manner with the substitution of the shear-wave parameters.

Other Parameters

The other viscoelastic parameters that can be directly calculated from these data are the bulk storage and loss moduli $K'$, $K''$; Young's storage and loss moduli $Y'$, $Y''$; and Poisson's ratio $v'$. The equations for calculating these parameters will be for the storage components. A set of analogous equations with the appropriate substitutions are used for the loss moduli. The bulk modulus is calculated by rearranging Equation 1:

$$K' = M' - 4/3 G' \quad (14)$$

Young's modulus is calculated by using the well-known interrelationships between elastic moduli:

$$Y' = 9 K' G'/(3K' + G') \quad (15)$$

Accordingly, Poisson's ratio is calculated by $$v' = (3K' - 2G')/2(3K' + G') \quad (16)$$

However, the calculation of the loss component of Poisson's ratio is not as straightforward. The equation for loss Poisson's ratio in terms of velocity and attenuation and moduli is:

$$v'' = \frac{\text{Tan}\frac{G''}{G'} - \text{Tan}\frac{M''}{M'}}{2\left(\frac{C_D}{C_S} - \frac{C_S}{C_D}\right)^2}$$

Some examples are presented of the types of plots that can be obtained from this apparatus.

Figure 7:
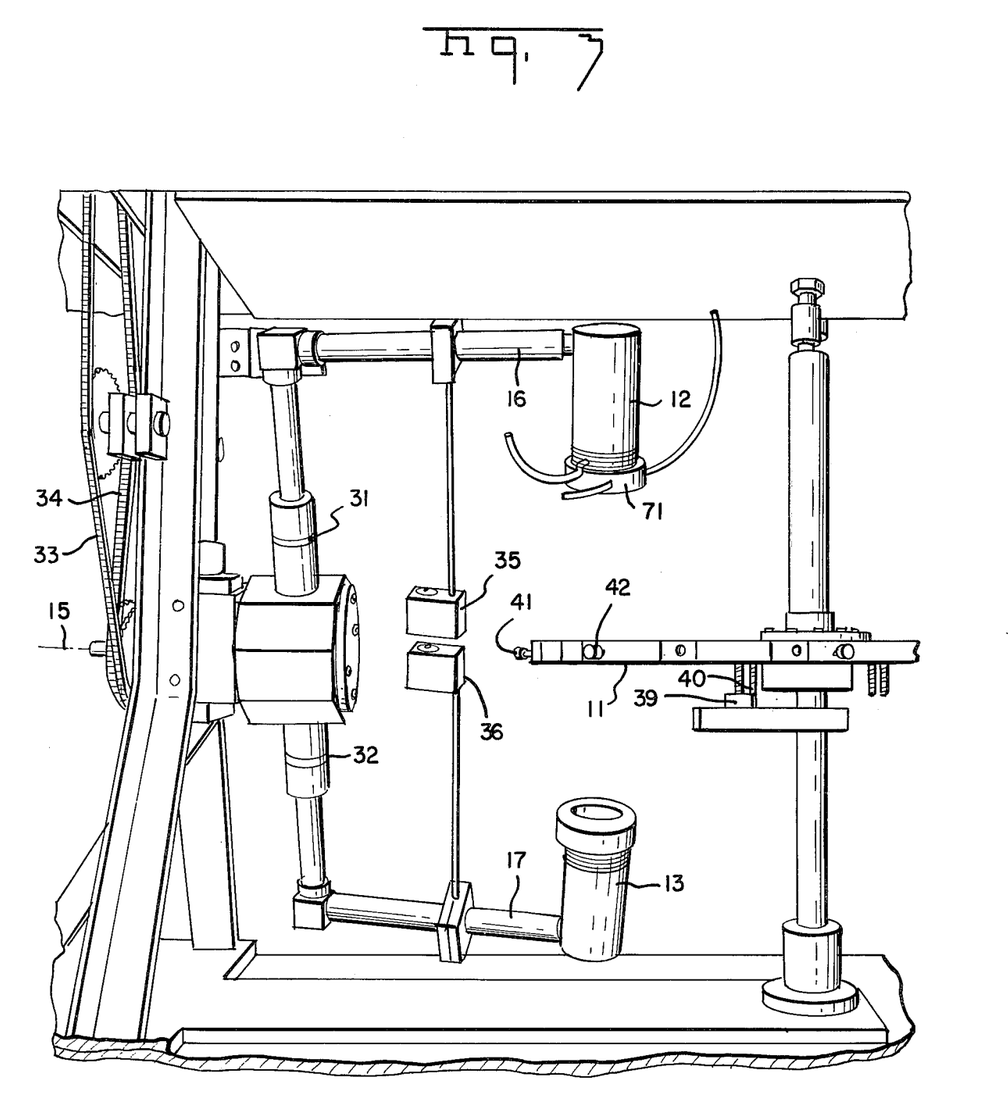
FIG. 7 is a plot of the storage moduli as a function of temperature and Poisson's ratio as a function of temperature.

FIG. 7 shows the normal temperature dependence of the storage moduli and Poisson's ratio at 2.4 MHz for a compressionmolded poly(vinyl chloride) (Firestone 965) homopolymer. The heating rate was 0.5 deg C/min.

Figure 8:
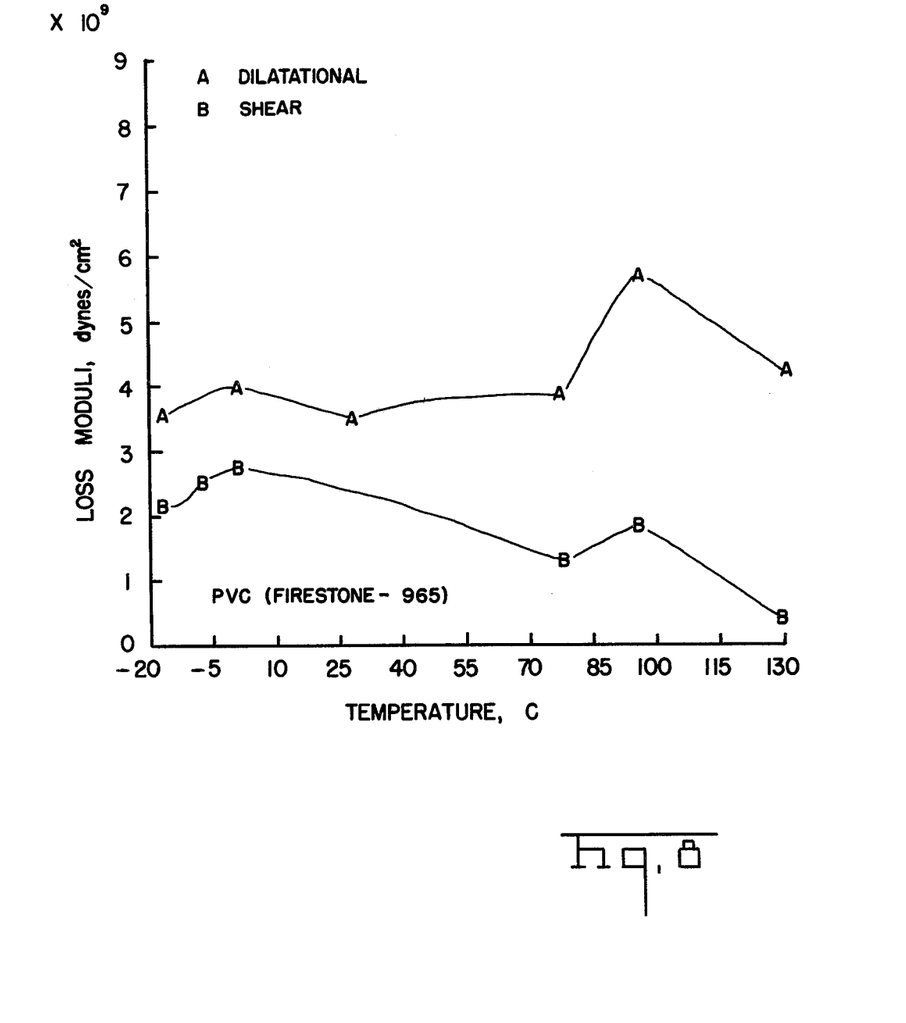
FIG. 8 is a plot of the dilatational and shear loss moduli as a function of temperature.

FIG. 8 shows the temperature dependence of the dilatational and shear-loss moduli for the same specimen. The 25° C. is the $\beta$-transition.

In a working embodiment of the invention, the inputs for the digital computer 29 were manually keyed into the machine. It will be apparent that the system can be completely automated to automatically process the measurements.

In the working embodiment, the digital computer was a model DEC-10 made by the Digital Equipment Corporation and the plotter 30 was made by the Benson & Lehner Company. Other general purpose minicomputers and microprocessors can be used. The manner in which such computers operate to perform the measurements described above will be apparent from the foregoing description and the user's manual for the particular computer used.

While a particular embodiment of the invention has been shown and described, various modifications are within the true spirit and scope of the invention. The appended claims are, therefore, intended to cover all such modifications.

What is claimed is:

1. A method of ultrasonically testing material comprising:
   mounting a specimen of said material in a specimen holder;
   immersing said specimen holder in a sound-conducting fluid;
   obtaining ultrasonic measurements with a transmitting transducer and receiving transducer supported in opposed orientation on opposite sides of said sample holder;
   rotating said transducers about an axis between said transducers;
   reorienting said transducers relative to said sample holder;
   obtaining new ultrasonic measurements with said transducers;
   repeating the steps of obtaining ultrasonic measurements for different temperatures of said fluid;
   measuring in situ the temperature dependent characteristics of said specimen at each temperature; and
   determining the intrinsic storage moduli and the intrinsic loss moduli of said specimens as a function of temperature from said ultrasonic measurements and from said temperature dependent characteristics.

2. The method recited in claim 1 wherein the step of measuring the temperature dependent characteristics of said specimen includes measuring the thickness of said specimen at each temperature.

3. The method recited in claim 1 wherein said material is a polymer material and wherein the step of measuring the temperature dependent characteristics includes measuring the mass density of said specimen at each temperature.

4. The method recited in claim 1 wherein said material is a polymer material and wherein the step of obtaining ultrasonic measurements includes:
   exceeding the shear wave critical angle from the rotation of said transducers and measuring the incident angle;
   measuring the dilatational and shear velocities of acoustic waves in said specimen; and
   determing the storage moduli of said specimen from the measured dilatational and shear velocities, incident angle and physical characteristics including specimen thickness and mass density.

5. The method recited in claim 4 further comprising:
   plotting said storage moduli as a function of the temperature at which said measurements were obtained.

6. The method recited in claim 4 wherein the step of measuring dilatational velocity includes:
   electronically measuring the transit time of an acoustic wave between said transmitting transducer and said receiving transducer when said transducers are orthogonally aligned with respect to said specimen to determine dilatational velocity.

7. The method recited in claim 6 further comprising:
   rotating said transducers about said axis past the shear wave critical angle; and
   electronically measuring said transit time above said critical angle to determine shear wave velocity.

8. The method recited in claim 7 wherein the measurement of dilatational velocity is determined from:

$$C_D = L[\tau_{TD} - (\tau_C - L/V_L)]^{-1}$$

wheren $C_D$ is said dilatational velocity, L is the thickness of said specimen, $\tau_{TD}$ is said transit time when said transducers are orthogonally aligned with respect to said specimen, $\tau_C$ is said calibration transit time and $V_L$ is the velocity of sound in said fluid.

9. The method recited in claim 8 wherein said shear velocity is determined from:

$$C_S = L_S[\tau_{TS} - (\tau_C - L_{fl}/V_L]^{-1}$$

where $C_S$ is said shear velocity, where $$L_S = L[1 - (A\sin\psi)^2]^{-\frac{1}{2}}$$

where $$A = [(\cos\psi - V_L(\tau_C - \tau_{TS})/L)^2 + \sin^2\psi]^{-\frac{1}{2}}$$

where $\psi$ in said incident angle, and where $$L_{fl} = L_S \cos(\phi - \psi),$$

where $\phi = \cos^{-1}(L/L_S)$.

10. The method recited in claim 1 wherein said material is a polymer material, and wherein said ultrasonic measurements are applied to a digital computer and wherein the attenuation coefficients of said materials are determined by iteratively solving transcendental equations in said digital computer.

11. The method recited in claim 1 further comprising:

reorienting said transducers relative to said specimen holder after each step of rotating by counter-rotating said transducers one with respect to the other.

12. The method recited in claim 11 wherein a first electric motor rotates said transducers and a second electric motor counter-rotates said transducers, said method further comprising:
driving said second electric motor in reverse while rotating to maintain alignment of said transducers.

13. Test apparatus for ultrasonically testing specimens immersed in a sound-conducting fluid comprising:
a specimen holder;
a first transducer for transmitting acoustic energy through said specimen holder;
a second transducer for detecting acoustic energy;
means for supporting said first and second transducers in opposed orientation with said specimen holder therebetween;
means for rotating said transducers about an axis between said transducers;
means for measuring the mass density of said specimens in situ at different temperatures; and
means for measuring the thickness of said specimen in situ at different temperatures.

14. The apparatus recited in claim 13 further comprising:
a potentiometer connected to said means for rotating so that the electrical output of said potentiometer indicates the angle of rotation of said transducers about said axis and the incident angle of said transducers to the specimen.

15. The apparatus recited in claim 13 further comprising:
a rotatable support surface;
a plurality of said specimen holders on said rotatable support surface;
alignment pins on said support surface; and
a switch engaged by said alignment pins, the output of said switch indicating when one of said specimen holders is aligned with said transducers.

16. The apparatus recited in claim 13 wherein said means for supporting comprises:
first and second arms counter-rotatable in planes parallel to said axis;
said first and second transducers extending orthogonally from the ends of said first and second arms respectively;
a first electric motor for rotating said means for supporting about said axis; and
a second electric motor for counter rotating said arms.

17. The apparatus recited in claim 16 and an alignment detector for indicating alignment of said arms and said orthogonally extending transducers in a plane, said alignment detector comprising:
a light source extending from one of said arms and oriented in said plane;
a photodetector extending from the other of said arms and oriented in said plane whereby said photodetector produces an output when said arms and said transducers are re-counter-rotated into said plane.

18. The apparatus recited in claim 13 wherein said transducers are mounted in fluid tight containers having a removable closure and a polymer gasket therefore;
solderless connectors in each of said containers for making electrical connections to said transducers; and
inserts for adapting the diameter of said transducers to the inside diameter of said containers whereby the transducers can be changed for making different frequency measurements.

19. The apparatus recited in claim 13 mounted in a tank containing a silicone fluid having low acoustic loss, low velocity, low viscosity and low viscosity/temperature coefficient.

20. The apparatus recited in claim 19 further comprising:
thermocouples mounted in said tank for measuring the temperature of said fluid.

21. The apparatus recited in claim 13 further comprising:
means for applying vacuum to the surface of one of said transducers to remove air bubbles therefrom.

22. The apparatus recited in claim 13 further comprising:
baffles mounted on said transducers for agitating said fluid to prevent thermal gradients therein.

23. Test apparatus for ultrasonically testing specimens immersed in a sound-conducting fluid comprising:
a specimen holder having a closed, air-tight chamber;
a first transducer for transmitting acoustic energy through said specimen holder;
a second transducer for detecting acoustic energy;
means for supporting said first and second transducers in opposed orientation with said specimen holder therebetween;
means for rotating said transducers about an axis between said transducers;
means for measuring the temperature dependent characteristic of said specimens in situ;
a manometer connected to said closed chamber for measuring the volume of said specimen; and
means for determining mass density from the measured weight and volume of said specimen.

24. The apparatus recited in claim 23 further comprising:
an air piston for pressurizing said chamber, said manometer being connected between said piston and said chamber; and
a valve for selectively connecting the end of the manometer connected to said piston to the atmosphere whereby the change in manometer reading over atmosphere indicates the volume of said chamber.

25. Test apparatus for ultrasonically testing specimens immersed in a sound-conducting fluid comprising:
a specimen holder;
a first transducer for transmitting acoustic energy through said specimen holder;
a second transducer for detecting acoustic energy;
means for supporting said first and second transducers in opposed orientation with said specimen holder therebetween;
means for rotating said transducers about an axis between sid transducers;
means for measuring the temperature dependent characteristic of said specimens in situ including:
a probe mounted to engage one surface of a specimen in said holder;
a d.c., linear-variable, differential-transformer, said probe extending through said transformer so that the electrical output of said transformer indicates the position of said probe; and
means for selectively engaging said probe with the surface of said specimen to measure the thickness of said specimen in situ.

* * * * *